United States Patent [19]

Van Hoye et al.

[11] Patent Number: 4,790,624
[45] Date of Patent: Dec. 13, 1988

[54] METHOD AND APPARATUS FOR SPATIALLY ORIENTING MOVABLE MEMBERS USING SHAPE MEMORY EFFECT ALLOY ACTUATOR

[75] Inventors: Michael Van Hoye, Anaheim; Geoffrey L. Taylor, Valencia; Hamid Saghatchi, Burbank, all of Calif.

[73] Assignee: Identechs Corporation, Dallas, Tex.

[21] Appl. No.: 926,357

[22] Filed: Oct. 31, 1986

[51] Int. Cl.⁴ .............................................. G02B 23/26
[52] U.S. Cl. ....................................... 350/96.26; 128/4
[58] Field of Search .................... 350/96.26; 148/402; 128/4, 785, 6; 337/139

[56] References Cited

U.S. PATENT DOCUMENTS

| | | | |
|---|---|---|---|
| 3,890,977 | 6/1975 | Wilson | 128/785 X |
| 4,205,293 | 5/1980 | Melton et al. | 337/139 X |
| 4,531,988 | 7/1985 | Todoroki et al. | 148/402 |
| 4,601,283 | 7/1986 | Chikama | 128/4 |
| 4,620,769 | 11/1986 | Tsuno | 128/6 X |

Primary Examiner—John D. Lee
Assistant Examiner—John Ngo
Attorney, Agent, or Firm—William L. Chapin

[57] ABSTRACT

A method and apparatus for spatially orienting a remote flexible member such as the tip of a borescope to point in a desired direction employs heating to its transition temperature a shape memory efffect SME alloy actuating element coupled to the tip and cable. In one embodiment, an elongated helical spring fabricated from an SME alloy such as NI—TI or CU—ZN—AL is longitudinally disposed between the remote end of a borescope cable, and the borescope tip. An electrical resistance wire heater in contact with the spring and energized by an electrical power source controlled by an observer at the near end of the cable is used to heat a selected part of the spring to the transition temperature of the SME alloy of which it is fabricated, producing a controlled deflection of the borescope tip to point in a direction directed by the observer.

42 Claims, 5 Drawing Sheets

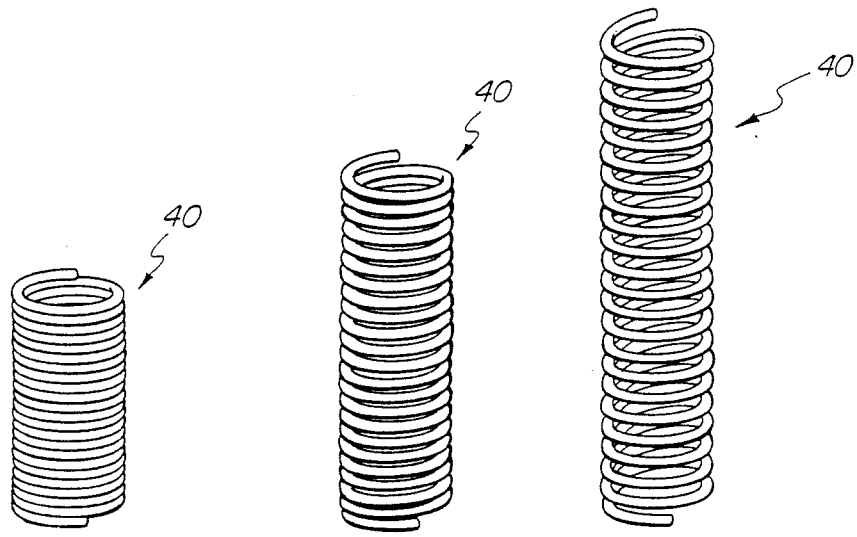
FIG. 1  FIG. 2  FIG. 3
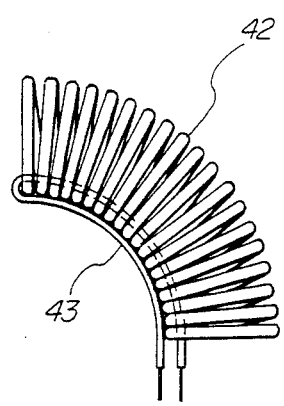
FIG. 4
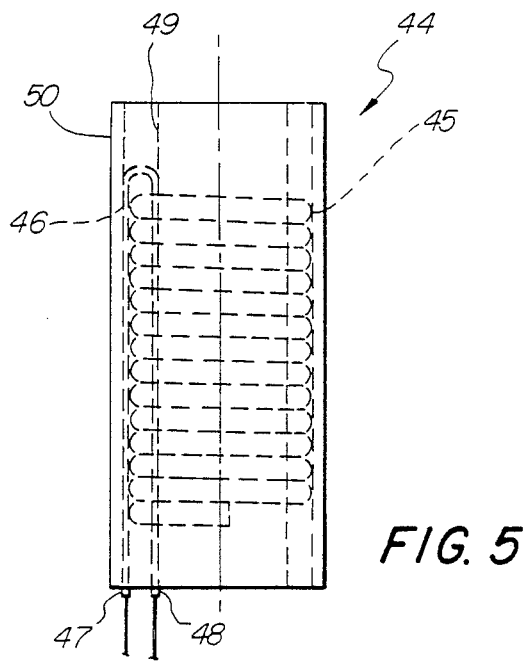
FIG. 5
 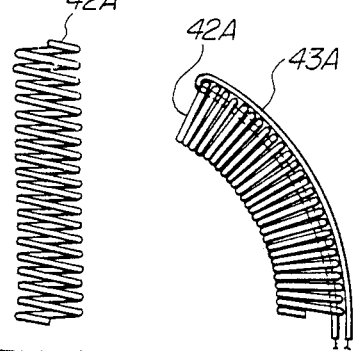
FIG. 4A  FIG. 4B  FIG. 4C
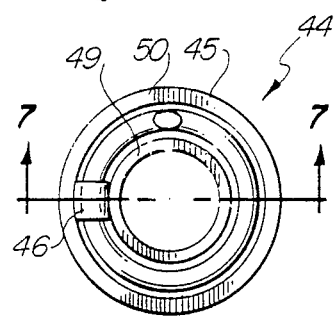
FIG. 6

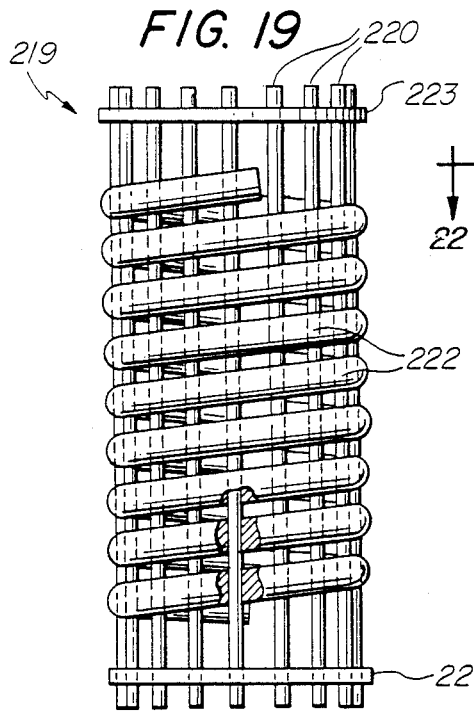
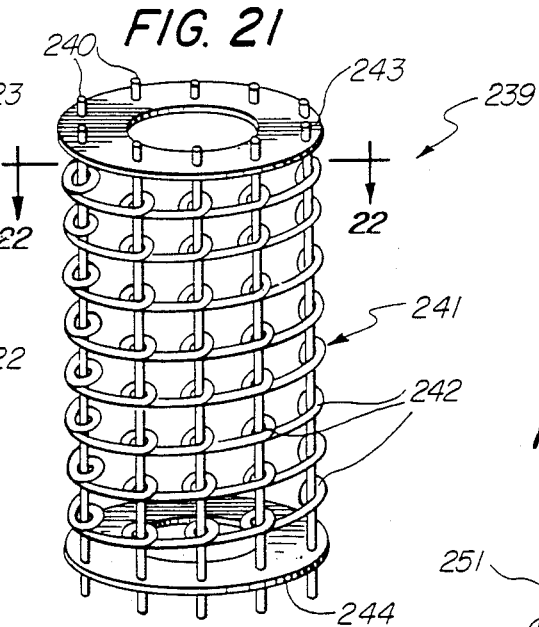
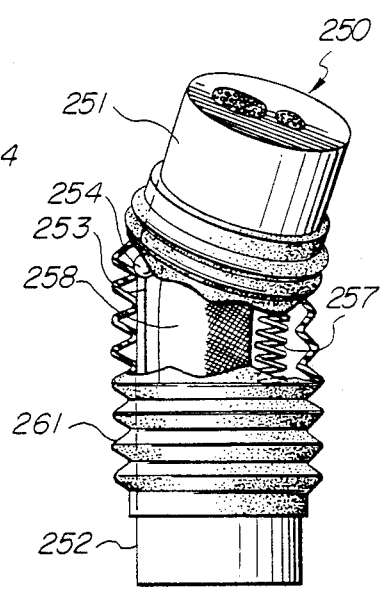
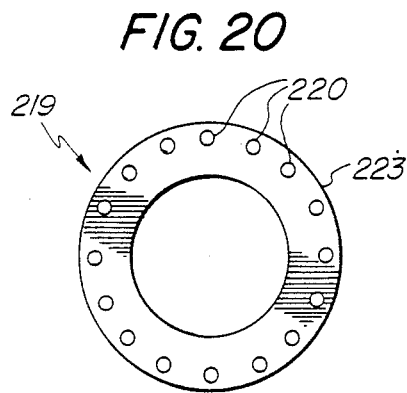
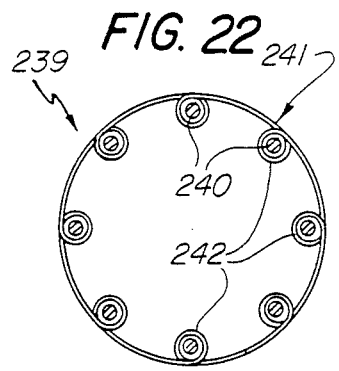
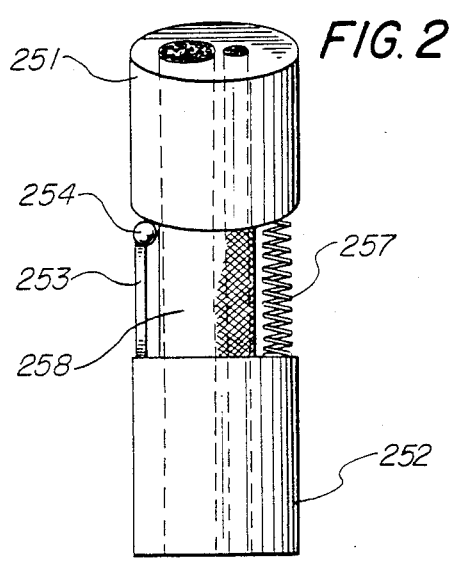
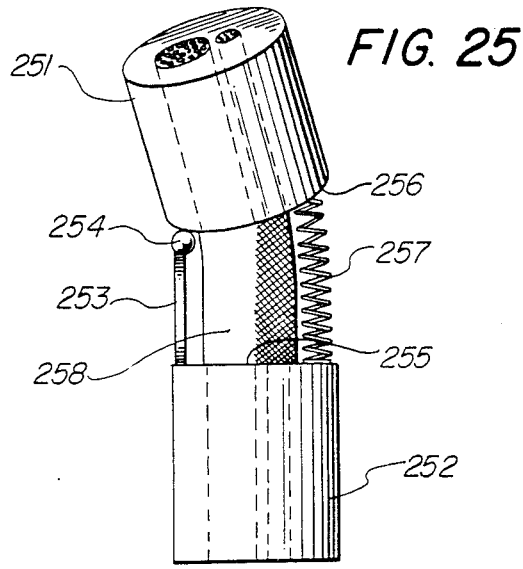

METHOD AND APPARATUS FOR SPATIALLY ORIENTING MOVABLE MEMBERS USING SHAPE MEMORY EFFECT ALLOY ACTUATOR

BACKGROUND OF THE INVENTION

A. Field of the Invention.

The present invention relates to methods and devices for rotating the movable end of an elongated member for the purpose of spatially orienting the longitudinal axis of the member end to point in a desired direction. More particularly, the invention relates to a method and apparatus for remotely articulating the distant end of a flexible borescope to point in a desired direction, thereby bringing a desired area within the field of view of the borescope.

B. Discussion of Background Art.

Borescopes are elongated optical devices capable of transmitting visual images to a remote observer. The devices are used to transmit images of objects near the distant end of the device to an observer at the near end of the device. This image transmitting capability permits an observer to perform a visual inspection of remote objects within the field of view of the far end of the device. Borescopes were first used to inspect the bores of guns, hence the name. Presently, borescopes are used to permit inspection of a large variety of objects located in remote, inaccessible or hazardous areas. Thus, they are used in such diverse applications as the inspection of turbine engines, human bodies, and nuclear reactors.

The first borescopes were essentially rigid, elongated tubular microscopes which employed a series of lenses to convey an image of an object in the field of view of a field lens at a remote end of the tube to an objective lens at the observer's end of the tube. Usually, means were also provided to illuminate the field of view of the borescope, as for example by a small lamp located near the remote end of the tube.

Most modern borescopes utilize flexible fiber-optic cables rather than lenses. The fiber-optic cables contain parallel bundles of fine transparent fibers, and transmit to one end of the cable an image of the area within the field of view of the opposite end of the cable.

Most fiber-optic borescopes have a flexible protective sheath covering the entire length of the cable. Typically, the sheath is made of a durable, abrasion resistant material such as woven metal. Also, most fiber-optic borescopes include within the sheath a second fiber-optic cable which is illuminated by a bright light source at the observer's end. The second cable transmits light to the remote end of the cable, which then illuminates the field of view of the imaging fiber-optic cable.

In a very recent development in flexible borescopes, a solid state television camera is contained within a borescope tip, eliminating the need for a fiber-optic image cable. The solid state camera sensor consists of a silicon chip less than ⅛" in diameter and having an array of light sensitive elements, arranged in a matrix. These devices, referred to as Charge Coupled Devices ("CCD's"), are imbedded in a borescope tip and produce a video signal capable of forming an image of each objects within the field of view of the CCD. The video signal is conducted by means of electrical wires within the borescope cable to a television monitor located at the observer's end of the cable.

The tips of some fiber-optic borescopes can be remotely manipulated by an observer at the viewing end of the borescope to position the axis of the imaging fiber-optic cable at a desired orientation, thereby bringing into its field of view a desired area of interest. These remotely manipulateable fiber-optic borescopes are referred to as articulated, articulating or articulateable borescopes. By applying tension to one or more flexible wires strung through the protective sheath and attached to a pivotable member near the remote end or head of the cable, the head may be tilted at an angle to the longitudinal axis of the cable. Such borescopes can have either one or two planes of articulation. The latter type permits aiming the head of the borescope to any point in a forward directed hemisphere (or larger portion of a sphere) centered around the head end of the cable.

A variety of structures permitting the bending of the remote end of an articulated conduit by an operator at the near end of the conduit have been disclosed. Examples of such articulation structures are disclosed in the following U.S. Patents:

Stegeman, U.S. Pat. No. 2,424,064, July 15, 1947, Illuminating Device

Ulrich, U.S. Pat. No. 3,071,161, Jan. 1, 1963, Bidirectional Flexible Segmented Tube Bazinet, U.S. Pat. No. 3,162,214, Dec. 22, 1964, Flexible Tubular Structures Stokes, U.S. Pat. No. 3,190,286, June 22, 1965, Flexible Viewing Probe for Endoscopic Use Maudinet, U.S. Pat. No. 3,301,588, Jan. 31, 1967, Remote Control Manipulation of Inaccessible Objects Marie, U.S. Pat. No. 3,326,620, June 20, 1967, Linked Wave Transmitting System for Light Waves Bazell, U.S. Pat. No. 3,572,325, Mar. 23, 1971, Flexible Endoscope Having Fluid Conduits and Control Takahashi, U.S. Pat. No. 3,583,393, June 8, 1971, Bendable Tube Assembly Takahashi, U.S. Pat. No. 3,669,098, June 13, 1972, Endotracheal Tube Fukaumi, U.S. Pat. No. 3,799,151, Mar. 26, 1974, Controllably Bendable Tube of an Endoscope Hosono, U.S. Pat. No. 3,998,216, Dec. 21, 1979, Bending Tube for Endoscope Tanaka, U.S. Pat. No. 4,108,211, Aug. 22, 1978, Articulated, Four-Way Bendable Tube Structure Hosono, U.S. Pat. No. 4,347,837, Sept. 7, 1982, Structure for Preventing the Breakage of End Portions of a Protective Covering for the Adjustable Bend Section of an Endoscope Ouchi, U.S. Pat. No. 4,351,323, Sept. 28, 1982, Curvable Pipe Assembly in Endoscope Sakuragi, U.S. Pat. No. 4,396,797, Aug. 2, 1983, Flexible Cable Sheldon, U.S. Pat. No. 3,060,972, Oct. 30, 1962, Flexible Tube Structure Siegmund, U.S. Pat. No. 4,290,421, Sept. 22, 1981, Fiberscope Wentzell, U.S. Pat. No. 4,575,185, Mar. 11, 1986, System for a Fiber-Optic Cable for Remote Inspection of Internal Structure of a Nuclear Steam Generator All of those articulation control structures disclosed in patents listed above which are useful for articulating flexible borescopes have a common characteristic; each of the structures employs pull wires anchored to the far end of the articulateable tube section, near the borescope tip. The wires run back through guides within the borescope cable, are longitudinally slidable within the guides, and terminate at a differential tension producing member operable by a user at the observation end of the borescope cable. A single pair of wires provides two-way articulateability in a single plane. By differentially varying the tension in the two control wires, the borescope tip can be tilted in either of two directions in a single plane. Two pairs of wires are required to provided articulateability in two perpendicular planes (four-way articulateability). The Siegmund patent discloses an improved articulation structure in which three longitudinally disposed pull wires spaced at 120 degree circumferential angles provided four-way articulateability.

Wentzell, in U.S. Pat. No. 4,575,185, Mar. 11, 1986, discloses the use of sealed, flexible chambers within a flexible tube assembly. The chambers contain fluids and are differentially pressurized to vary the buoyancy of the tube assembly in a liquid environment, thereby permitting the remote end of the tube to be bent in a desired direction. By this means, the aim point of a fiber optic inspection cable contained coaxially within the flexible tube assembly may be controlled when the assembly is inserted into a liquid filled chamber such as a nuclear steam generator.

The pull wires used by all general purpose borescope articulation structures disclosed in the prior art impose certain limitations on the performance capabilities of borescopes equipped with those articulation structures. For example, the friction between the pull wires and their enclosing guide tubes becomes troublesome when long borescope cables are required. Also, the weight added to the borescope cable by the lengths of 2, 3 or 4 stout pull wires can make manipulation of long cables quite difficult. As a practical matter, the above cited problems with existing pull-wire borescope articulation structures imposes an upper limit on the length of practical articulating borescopes.

The present invention was conceived of to provide an improved method of remotely manipulating a flexible cable tip. In particular, a goal of the present invention was to provide an improved method and apparatus for articulating borescope cables which overcome limitations inherent in prior art borescope articulation structures.

OBJECTS OF THE INVENTION

An object of the present invention is to provide a method and apparatus for spatially orienting the longitudinal axis of a movable member from a remote location.

Another object of the invention is to provide a method and apparatus for articulating the movable tip of a flexible borescope to point in a desired direction without the requirement for pull wires or other moving elements spanning the length of the borescope cable.

Another object of the invention is to provide a method and apparatus for providing a substantial articulation force to the head of a flexible borescope by lightweight actuation means.

Another object of the invention is to provide a versatile and lightweight actuator for deflecting a movable member to a desired spatial orientation.

Various other objects and advantages of the present invention, and its most novel features, will be particularly pointed out hereinafter in connection with the appended claims.

It is to be understood that although the invention disclosed herein is fully capable of achieving the objects and providing the advantages mentioned, the structural and operational characteristics of the invention described herein are merely illustrative of the preferred embodiments. Accordingly, we do not intend that the scope of our exclusive rights and privileges in the invention be limited to the details of construction and operation described. We do intend that reasonable equivalents, adaptations and modifications of the various embodiments and alternate forms of the present invention which are described herein be included within the scope of the invention as defined by the appended claims.

SUMMARY OF THE INVENTION

Briefly stated, the present invention comprehends a novel and highly effective actuator method and apparatus for remotely deflecting the head of a flexible borescope to point in a desired direction. The novel actuators according to the present invention employ rods, springs and other structural forms fabricated from a special class of alloys known in the art as Shape Memory Effect ("SME") alloys. Nickel-titanium ("NITINOL") alloys and copper-zinc-aluminum or copper-zinc-tin ("SME BRASS") constitute the two main classes of SME alloys. When a structure fabricated from one of these alloys is heated above a certain temperature referred to as the transition temperature for the particular alloy, the structure changes form rapidly from one shape to a different, "memory" state, which has been previously imprinted on the structure. Recovery of the memory shape is accompanied by the production of a substantial force. In the present invention, that force is used to bend the tip of a flexible borescope.

In some particularly novel and useful embodiments of the present invention employing actuator elements fabricated from SME alloys, an element is differentially heated to cause the element to bend in a selected direction. One embodiment of the novel actuator according to the present invention includes a helical spring fabricated from a SME alloy and fitted coaxially within a flexible borescope cable, just rearward of the rigid tip of the borescope. A plurality of elongated heating strip elements in thermal contact with the cylindrical side walls of the spring span the length of the spring. The heating elements are selectably energizable, and spaced at regular circumferential angles around the spring. Energizing a heating strip sufficiently to raise the temperature of part of the spring to its transition temperature causes the diametrically opposed longitudinal side of the spring to uncoil, deflecting the enclosing borescope cable towards the energized strip.

Cooling the strip by convection or conduction relieves the internal stress in the spring which caused it to assume its memory shape when the spring was heated to the transition temperature of the spring alloy. With the stress decreased, the spring may be forced to assume its quiesient, undeflected shape by an auxiliary force producing element, such as conventional spring. Alternatively, the SME alloy spring may be trained to recover a second, quiescent memory shape upon being cooled below its transition temperature. This latter method elimates or reduces the requirement for auxiliary bias springs.

BRIEF DESCRIPTION OF THE DRAWINGS

FIG. 1 is a perspective view of a helical spring fabricated from SME alloy wire and comprising one element common to several different embodiments of the borescope articulation apparatus actuators according to the present invention.

FIG. 2 is a perspective view of the spring of FIG. 1 in which the spring is at a temperature above the lower end of the transition or memory recovery temperature range of the shape-memory-effect ("SME") alloy of which the spring is fabricated.

FIG. 3 is a view of the spring at a temperature above the upper end of the memory recovery temperature range.

FIG. 4 is a perspective view of the spring of FIG. 1 in which a longitudinal zone along one side of the spring has been differentially heated to a temperature above the transition temperature.

FIG. 4A is a perspective view of an SME alloy helical spring in which the high temperature memory shape is that of a medium pitch helix.

FIG. 4B is a perspective view of the spring of FIG. 4A in which the spring has been stretched longer than its high temperature memory shape.

FIG. 4C is a perspective view of the spring of FIG. 4B in which a longitudinal zone along one side of the spring has been heated differentially to a temperature above the transition temperature of the SME alloy of which the spring is fabricated.

FIG. 5 is a side elevation view of a one-way, single plane SME alloy borescope articulation actuator according to the present invention.

FIG. 6 is a front end view of the actuator of FIG. 5.

FIG. 19 is a side elevation view of a modified version of the actuator spring of the type shown in FIGS. 5, 9, and 11, in which straight heating elements run through longitudinally aligned holes in the coils of the spring.

FIG. 20 is a front end view of the apparatus of FIG. 19.

FIG. 21 is a perspective view of another modification of the actuator spring of the type shown in FIGS. 5, 9, and 11, in which each coil of the spring contains a plurality of regularly and circumferentially spaced loops which encircle longitudinally disposed heating elements.

FIG. 22 is a front end view of the apparatus of FIG. 21.

FIG. 23 is a side elevation view of a borescope cable articulation apparatus according to the present invention, which employs a single SME alloy actuator spring.

FIG. 24 shows the apparatus of FIG. 23 in which the actuator spring has been heated to a temperature above the lower temperature limit of its transition temperature.

FIG. 25 shows the apparatus in FIG. 23 in which all of the coils of the actuator spring have been heated to a temperature above the upper temperature limit of its transition temperature range.

DESCRIPTION OF THE PREFERRED EMBODIMENTS

Introduction

Figure 7:
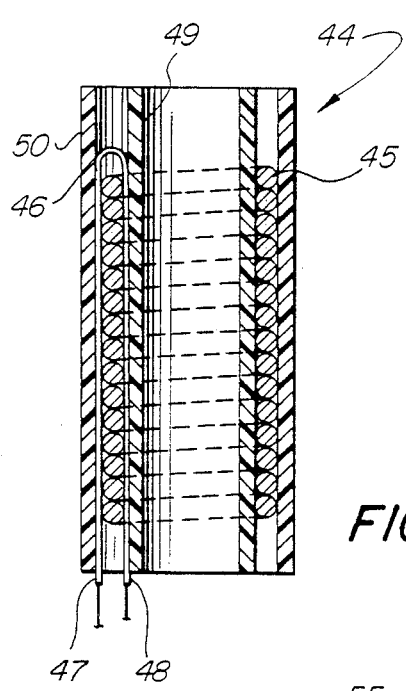
FIG. 7 is a longitudinal sectional view of the actuator of FIG. 5, taken along line 7—7 of FIG. 6.

The novel borescope articulation devices according to the present invention employ actuators made of shape-memory-effect ("SME") alloys. These alloys have some rather unusual properties. For that reason, a more complete understanding of the operation of the novel articulation devices to be described can be facilitated by a brief description of the properties of SME alloys, and is presented below.

Shape-memory-effect alloys are metals or polymers which, if plastically deformed at one temperature, will recover their original shape on being raised to a particular higher temperature, called the transition temperature. The original shape which is "remembered" by the metal upon being heated above the transition temperature is imprinted in the metal by forming the metal into that shape at a temperature far above the transition temperature.

Metal alloys displaying a shape-memory-effect suitable for our actuators include nickel-titanium (NITINOL) and copper-nickel-aluminum or copper-zinc-aluminum (SME brass). These alloys have one particular crystal structure called martensite at a temperature below the transition temperature for the particular alloy, and a different crystal structure, called austenite, above the transition temperature.

To "train" a SME alloy actuator element to remember a particular shape configuration, the element is first heated to a high temperature sufficient to anneal the element, typically 500° C. to 800° C. While held at this temperature, the part is mechanically stressed by external clamping or similar means to produce a desired shape. During this operation, the metal assumes what is called the parent or beta phase. The part is subsequently cooled to a temperature at which the internal structure of the metal is transformed into an orderly crystalline state referred to as a quench induced martensitic state. The martensitic transformation starts at a temperature referred to as $M_S$, and finishes at a lower temperature referred to as $M_F$. These temperatures vary as a function of alloy composition. $M_S$ is reported to vary between $-273°$ C. to $+100°$ C. for NI-TI binary alloys, and $-105°$ to $+300°$ C. for CU-ZN-AL and CU-NI-AL ternaries.

After an actuator element has been trained as described above, the element can be mechanically stressed inelastically to a deformed state having substantial residual strain. If the element is now heated to a temperature referred to as $A_S$, the internal crystal structure begins to change from martensitic to austenitic, a process which is complete at a higher temperature referred to as $A_F$. During this process, the element recovers its original "trained" shape, and may exert a substantial force in doing so. $A_S$ is above $M_S$, and the range between $A_S$ and $A_F$ is typically 20 to 30 degrees centigrade. The temperature range between $A_S$ and $A_F$ may be defined as a memory recovery range. Typically, this range is about 20° C., although it has been reported to be as low as 6° C. and as high as 80° C. for certain alloy compositions.

The training process described above produces what is referred to as a one-way memory effect. SME elements having a two-way memory effect are more useful for use in some of our articulation mechanisms. In an SME alloy element having a two-way memory, the element transforms into its initially imprinted shape when its temperature is raised to $A_F$. Additionally, however, the element transforms into a second memory shape when cooled below $M_S$.

To imprint a two-way memory on an SME alloy element, the first memory shape is imprinted on the element exactly as has been described above for the one-way training process. The element is then cooled below $M_S$, mechanically stressed to a second memory state, producing what is referred to as a stress induced martensitic transformation. The part is then heated to its austenitic transition temperature ($A_S$ to $A_F$), at which time it assumes its first memory shape. Next, the part is cooled below $M_S$ while being stressed to conform to the second memory shape. This process is then cyclically repeated until memory of the second shape has been imprinted on the element. When imprinted with two-way memory, the element will assume the first memory shape when heated above the transition temperature of the alloy, and assume the second memory shape when cooled below the transition temperature.

DETAILED DESCRIPTION

FIGS. 1 through 4 show a helical spring comprising one element common to several different embodiments of the borescope articulation apparatus according to the present invention. The spring 40 illustrated in the Figures is fabricated from a particular SME alloy consisting of 70% copper, 25% zinc and 5% aluminum. This composition has a martensitic transformation temperature $M_S = -64°$ C., and a memory recovery temperature range extending from $A_S = 40°$ to $A_F = 77°$.

Spring 40 is first trained at high temperatures into the large pitch, open helix shown in FIG. 3, and compressed as shown in FIG. 1 at a temperature below $M_F$.

In FIG. 1, spring 40 is shown at a temperature below temperature $A_S$ at which a transition between the martensitic state and the austenitic memory state of the SME alloy begins as the temperature of the metal is raised. For the particular memory recovery temperature range of the specified alloy, FIG. 1 illustrates the condition of spring 40 at ambient temperature.

In FIG. 2, the temperature of spring 40 has been raised to a temperature midway between $A_S$ and $A_F$. At this temperature, transition of the spring to its memory state shown in FIG. 3 has begun.

In FIG. 3, spring 40 has been heated to a temperature equal to or above $A_F$. At this temperature, the spring has completely recovered its memory position, i.e., the relatively elongated, large-pitch position.

If spring 40 had been given only one-way training prior to raising its temperature to $A_F$, cooling the spring back to ambient temperature would have no effect on the shape of the spring. Thus, spring 40 would remain in the position shown in FIG. 3 when cooled. However, if spring 40 has previously been cycled through a sufficient number of heating and cooling cycles in which the spring has been externally stressed to the compressed position shown in FIG. 1, thereby effecting two-way training of the spring, it will be restored to the second memory position shown in FIG. 1, upon cooling below the transition temperature.

Structures made of SME alloys, such as the spring 40 shown in FIG. 1 through 3, have certain characteristics which are desirable for actuators in general, and for our novel borescope articulation mechanism in particular.

A particularly important characteristic of SME alloy elements is the great force which can be exerted by the element in recovering its high temperature memory state when raised above the transition temperature. For example, the amount of force exertable by a SME alloy wire in recovering its high temperature, parent phase memory shape is typically 50,000 lbs. per square inch; approximately 200 times the force that can be exerted by expansion and contraction of a bimetallic element of the same weight. Also, the permissible strain deformation for 100% shape recovery is much larger than ordinary metals. Thus, typical steel spring material can be deformed elastically only about 1%, while copper based SME alloys can be deformed 3–4%, and Ni—TI alloys 6% to 8%.

Another important characteristic of SME alloys which makes them desirable for our actuators is the rapid recovery of the high temperature memory state of elements fabricated from the alloys. Typically, the propagation velocity of this change approximates the speed of sound in the material, i.e., is thousands of feet per second. A SME alloy element which has had its temperature raised above the transition temperature and recovered its high temperature memory state recovers its low temperature memory state at a generally slower rate, and with the production of much less force than when recovering its high temperature memory state. These factors must also be considered in the design of SME alloy actuators.

Actuator elements such as the spring 40 of FIGS. 1 through 3 can be useful for our purposes even with one-way training. Thus, a conventional spring could be used to bias spring 40 to its compressed state shown in FIG. 1. When the SME alloy spring 40 is heated to its transition temperature, the substantial extensional force of the spring can be sufficient both to overcome the compressional bias of the conventional spring, yet perform substantial external work on the object to be moved by the extension of the SME alloy actuator spring. When the SME alloy spring 40 is cooled below its transition temperature, the force exerted by the bias spring can return the SME alloy spring to its quiescent, compressed state.

Some embodiments of our novel borescope articulation mechanism to be described employ one-way or two-way SME alloy actuator elements that are uniformly heated or cooled to an appropriate temperature, as has been described above. Other embodiments of our invention employ the particularly novel concept of differentially heating or cooling a selected portion of a SME alloy actuator element to produce spatially orientable articulation mechanisms of great versatility.

The operational concept of one of our differentially heated SME alloy actuator elements is illustrated in FIG. 4. FIG. 4 shows a helical spring 42 made of an SME alloy. Spring 42 is first trained at high temperatures to assume the form of an elongated, large pitch, open helix, such as shown in FIG. 3. The low temperature shape of spring 42 is that of a closed helix in which the pitch is equal to the vertical height or diameter of the wire from which the spring is fabricated, i.e., with adjacent coils of the spring touching, as shown in FIG. 1. The low temperature shape can be either a second trained state, or a shape maintained by auxiliary spring bias means If SME alloy spring 42 were heated uniformly to the transition temperature of the alloy, it would assume the form shown in FIG. 3. However, if only part of the spring 42 is heated, as for example a longitudinal zone heated by an elongated rectangular strip heater 43 placed in thermal contact with the zone, the spring assumes a different shape. As shown in FIG. 4, the coils of the spring 42 remain in contact in the heated zone, and are spread apart in the diametrically opposed longitudinal zone. Moreover, the originally cylindrical shape of the spring 42 is deformed into a bent tubular shape, which is concave towards the strip heater 48. The reason for this somewhat unexpected deformation of spring 42 upon differentially heating a longitudinal zone of the spring can be explained as follows.

When a selected longitudinal zone of the spring 42 is heated to its transition temperature, the heated portion recovers its high temperature memory shape. This shape is one in which the helix angle between adjacent loops of the spring 42 is larger, as shown in FIG. 3, than the low temperature helix angles, as shown in FIG. 1. However, the loops of the spring 42 in the unheated zone tend to maintain their low temperature, small helix angles. For these large and small angles to exist simultaneously in diametrically opposed longitudinal zones of the differentially heated spring, the spring must deform as shown in FIG. 4. In this deformed state, the maximum separation of adjacent coils is in a longitudinal zone diametrically opposed to the heated longitudinal zone.

The operation of another differentially heated SME actuator element is illustrated in FIGS. 4A through 4C. As shown in FIG. 4A, a helical spring 42A made of an SME alloy has been trained at high temperature to assume the form of an elongated, medium pitch, relatively open helix. The low temperature shape of spring 42A is that of a large pitch, open helix as shown in FIG. 4B. The low temperature shape can be either a second trained state, or a shape maintained by auxiliary spring bias means.

If SME alloy spring 42A were heated uniformly to the transition temperature of the alloy, it would assume the form shown in FIG. 4A. However, if only part of the spring 42 is heated, as for example by a longitudinal zone heated by an elongated rectangular strip heater 43A placed in thermal contact with the zone, the spring assumes a different shape. As shown in FIG. 4C, the coils of spring 42 spread apart in the heated zone, and contract towards one another in the diametrically opposed longitudinal zone. Moreover, the originally cylindrical shape of the spring 42A is deformed into a bent tubular shape, which is convex towards the strip heater 43A.

The explanation for the behavior of the spring 42A as depicted in FIG. 4C is as follows: When a selected longitudinal zone of the spring 42A is heated to its transition temperature, the heated portion recovers its high temperature memory shape. This shape is one in which the helix angle between adjacent loops of the spring 42A is smaller, as shown in FIG. 4B, than the low temperature helix angles, as shown in FIG. 4B. However, the loops of the spring 42A in the unheated zone tend to maintain their low temperature, large helix angles. For these large and small angles to exist simultaneously in diametrically opposed longitudinal zones of the differentially heated spring, the spring must deform as shown in FIG. 4C. In this deformed state, the maximum separation of adjacent coils is in the heated longitudinal zone.

A basic embodiment of our novel actuators for borescope articulation utilizing differential heating of a selected zone of a SME alloy helical spring is shown in FIGS. 5 through 7.

Actuator 44 shown in FIGS. 5 through 7 is useful for bending flexible members, such as the flexible sheath of a borescope rearward of the tip or head of the borescope. The basic version of this embodiment of our novel actuator is capable of tilting or deflecting a borescope head in a single plane.

For purposes of facilitating an understanding of our invention, one particular embodiment of our novel articulation mechanism actuator will be described in some detail. These details are for illustration purposes only, and should not be interpreted as limiting.

Referring now to FIGS. 5 through 7, actuator 44 includes a helical spring 45 fabricated of an SME alloy. The SME alloy spring 45 has been trained to give it at least a one-way, high temperature memory shape in which the pitch of the spring is substantially large, thereby resulting in an elongated, open spring. As shown in FIG. 5, at temperatures below the transition temperature of the SME alloy of which spring 45 is fabricated, adjacent coils of the spring are in longitudinal contact Thus, in the low temperature shape configuration, spring 42 has a minimum pitch, equal to the diameter of the SME alloy wire from which the spring is fabricated.

Preferably, spring 45 has been impressed with memory of its low temperature, fully compressed shape prior to its incorporation into actuator 44. Such two-way memory training may be accomplished as described above. As an alternative to two-way training, spring 45 may be constrained at low temperatures to assume a fully compressed state by any suitable biasing spring, made of conventional spring materials.

In our tests of an actuator of the type shown in FIGS. 5 through 7, we used a helical spring 45 fabricated from 0.115" diameter wire made of an SME alloy consisting of 70% copper, 25% zinc and 5% aluminum. The inner diameter of the helical spring 45 was approximately $\frac{5}{8}$", and the outer diameter was approximately $\frac{7}{8}$". With the spring 45 at its low temperature shape, the spring was fully compressed to a length of approximately $1\frac{3}{8}$". When heated to temperatures in the memory recovery temperature range of $A_S=104°$ F. to $A_F=170°$ F., spring 45 expanded to its high temperature memory shape, a large pitch helix having a length of approximately 3 inches.

As may be seen best by referring to FIG. 7, a heating element 46 loops around a desired longitudinal zone of helical spring 45. In our example actuator we used a rubber clad, resistance wire heating strip approximately 3 inches long by $\frac{1}{2}$ inch wide. Connection leads 47 and 48 extending from opposite ends of heating element 46 connect to the resistance wire heaters within the element, and permit electrical current to be conducted to the heating element. A hollow rubber tube 49 of approximately $\frac{1}{2}$" O.D. fits coaxially inside helical spring 45. The tube 49 keeps that half of the heater strip 46 which is inside the helical spring 45 in snug thermal contact with the adjacent inner longitudinal region of the spring. A flexible cylindrical jacket 50 fits coaxially over the outer length of heater strip 46 and helical spring 45, urging the outer length of the strip into intimate thermal contact with the adjacent outer longitudinal region of the spring.

Figure 8:
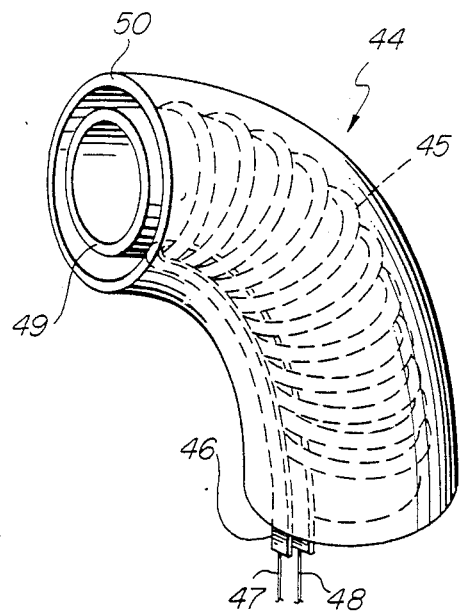
FIG. 8 is a perspective view of the actuator of FIG. 5 in which a heating element comprising part of the actuator has been energized sufficiently to heat a longitudinal zone of the actuator above the transition temperature of the SME alloy.

When one longitudinal zone of spring 45 is heated to its transition temperature by conducting electrical current into leads 47 and 48 of heating element 46, actuator 44 bends towards the heated zone as shown in FIG. 8. When current flowing into heating element 46 is discontinued, the heated longitudinal zone of spring 45 cools by convection and conduction, ultimately reducing the temperature of the zone below the transition temperature of the alloy. At this point, the shape of spring 45 recovers its low temperature memory shape or spring biased shape, as shown in FIG. 5.

In our tests of an actuator which we constructed, similar in appearance to the actuator shown in FIGS. 5 through 7, we were able to achieve angular defections of approximately 45 degrees with 20 watts of electrical power into heating element 46. When the actuator 44 was thus heated, allowing spring 45 to cool by natural conduction and convection resulted in recovery of the springs undeflected, compressed memory shape in approximately 7 seconds. Blowing room temperature air through tube 49 at a flow rate of approximately 5 cubic feet per minute reduced the low temperature memory shape recovery time to approximately one second.

It would be possible to decrease this recovery time further by decreasing the thermal resistance between the air flow channel within tube 49 and spring 45 and heating element 46. This could be achieved by perforating the walls of tube 49. The rate of recovery of the low temperature memory shape could also be increased by using colder air, nitrogen, or carbon dioxide gas, or liquids flowing through tube 49.

Figure 10:
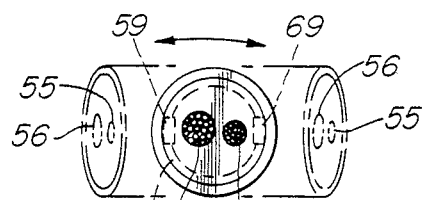
FIG. 10 is a front end view of the apparatus of FIG. 9, showing alternate articulated positions in phantom.
Figure 9:
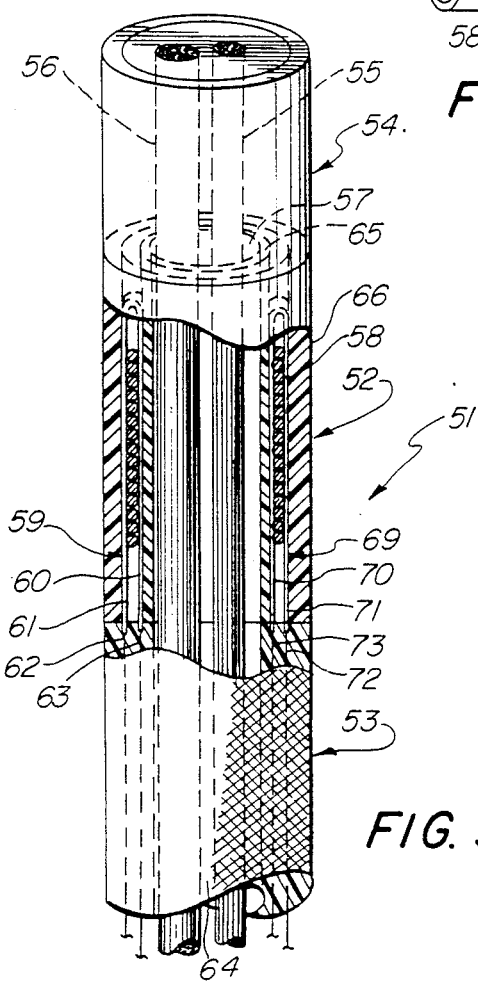
FIG. 9 is a side elevation view of a two-way, single plane SME alloy borescope cable articulation actuator joined with a borescope cable and head to form a complete articulateable borescope.

An embodiment of our borescope articulation apparatus employing an actuator similar to our novel actuator shown in FIGS. 5 through 7 is shown in FIGS. 9 and 10.

FIGS. 9 and 10 show a borescope articulation apparatus 51 including a generally cylindrical shaped, hollow actuator 52 coaxially aligned with and longitudinally positioned between the end of a borescope cable 53 and a borescope tip or head 54. A flexible, coherent, fiber-optic image guide 55 and a flexible, incoherent fiber-optic light guide 56 are shown running longitudinally through the borescope cable 53, through a hollow interior channel 57 of actuator 52, and through the borescope tip 54. Apertures are provided in the disc-shaped end plate of the borescope tip 54 to provide an entrance aperture for the fiber-optic image guide 55, and an exit aperture for the fiber optic-light guide 56. The specific details of the borescope cable and head recited above are by way of example only. It is to be understood that our novel articulation method and apparatus could be advantageously used for spatially orienting other flexible inspection devices, such as borescopes having an integral CCD (Charge Coupled Device) camera in the borescope head.

Actuator 52 includes a helical spring 58 fabricated of an SME alloy. The spring 58 has been trained to give it at least a one-way, high temperature memory shape in which the pitch of the spring is substantially large, thereby resulting in an elongated open spring when the spring is heated above the transition temperature of the SME alloy.

In its quiescent, low temperature state, spring 58 is fully compressed, as shown in FIG. 9. Preferably, spring 58 has been imprinted with a second, low temperature memory shape in which the spring is fully compressed. Alternatively to this two-way memory training, spring 58 can be biased to a quiescent compressed state by auxiliary spring means.

As shown in FIGS. 9 and 10, a flexible, elongated, rectangular strip heater 59 loops around a longitudinal zone of the helical spring 58. One half 60 of the heater strip 59 is adjacent to the inner concave side of the helical spring 58, while the other half 61 of the heater strip is adjacent to the outer, convex side of the spring strip. Strip heater 59 has resistance wire heating elements within an elastomeric, insulating matrix made of synthetic rubber or similar flexible, heat resistant material. Conductor leads 62 and 63 extending out from either transverse end of the heater strip 59 connect to the internal resistance wire heaters, and permit electrical current to be conducted to the heaters from an external power source. Conductor leads 62 and 63 run rearward from the actuator 52 through a conduit 64 in cable 53 to an external source of electrical power controllable by an operator situated at the viewing end of the borescope cable.

A hollow, flexible tube 65 fits coaxially within helical spring 58. The tube 65 keeps inner half 60 of heater strip 59 in snug thermal contact with the adjacent concave, longitudinal region of the spring 58. Preferably, tube 65 is made of an elastic, heat resistant material such as synthetic rubber. The tube 65 is preferably made at least as long as the maximum extended length of spring 58, and positioned in a longitudinally centered position within the spring. Thus, the tube 65 will continue to urge the entire length of the inner half 60 of strip heater 59 against the adjacent inner portion of spring 58, even when the spring is elongated to its maximum length.

A flexible cylindrical jacket 66 of approximately the same length as the tube 65 fits coaxially over the outer half 61 of the heater strip 59 and helical spring 58. While providing a protective outer cover for actuator 52, jacket 66 also urges the outer half 61 of the heater strip 59 into intimate thermal contact with the adjacent region of the spring 58. Neither jacket 66 nor core tube 65 forms such a tight circumferential fit with respect to the spring 58 and the heater strip 59 as to unduly impede the longitudinal expansion and contraction of the spring.

The structure of the borescope articulation apparatus 51 described to this point is capable of articulating the borescope tip 54 towards the strip heater 59, when the latter is electrically energized. The tilted position of the borescope tips is shown in phantom in FIG. 9. When the strip heater 59 is de-energized and allowed to cool, the borescope tip 54 returns to it normal, undeflected position in longitudinal alignment with actuator 52. As has been described above, return of the actuator spring 58 to its undeflected position is effected by recovery by the cooled spring of its second, compressed memory shape, or by auxiliary bias spring means.

The articulation capability of the apparatus 51 described thus far may be referred to as one-way (in direction) not to be confused with one-way or two-way memory), one plane. Here one-way means that the borescope tip controlled by the articulation apparatus may be bent in one direction from a central neutral position, and back to the neutral position, all while lying in a single plane. If, in addition to one-way deflection in a single plane, the actuation apparatus of 51 is given the capability of being rotated around its longitudinal axis to any position in a circle, the tip 54 of the borescope may be aimed at any point in a region approaching the size of a hemisphere centered around the tip.

Whether combined or not with a rotation capability, the borescope articulation apparatus 51 as described above represents an important advancement over existing borescope articulation devices. The novel apparatus described completely eliminates the need for moving pull cables and articulation members employed by all prior art general purpose borescope articulation devices. Thus, there is no upper limit to the length of articulateable borescopes constructed according to the present invention.

The borescope articulation apparatus 51 shown in FIGS. 9 and 10 can be given a two-way articulation capability by the addition of a second flexible strip heater. Thus, as shown in the figures, a second strip heater 69 identical in structure and function to strip heater 59 may be included in the construction of actuator 52. The strip heater 69 includes an inner half 70, an outer half 71, and current conductor leads 72 and 73 identical in structure and function to corresponding elements 60, 61, 62 and 63 of the strip heater 59. Energization of the strip heater 69 causes the borescope head to tilt exactly as has been described above for the energization of strip heater 59, but in the opposite direction.

Figure 11:
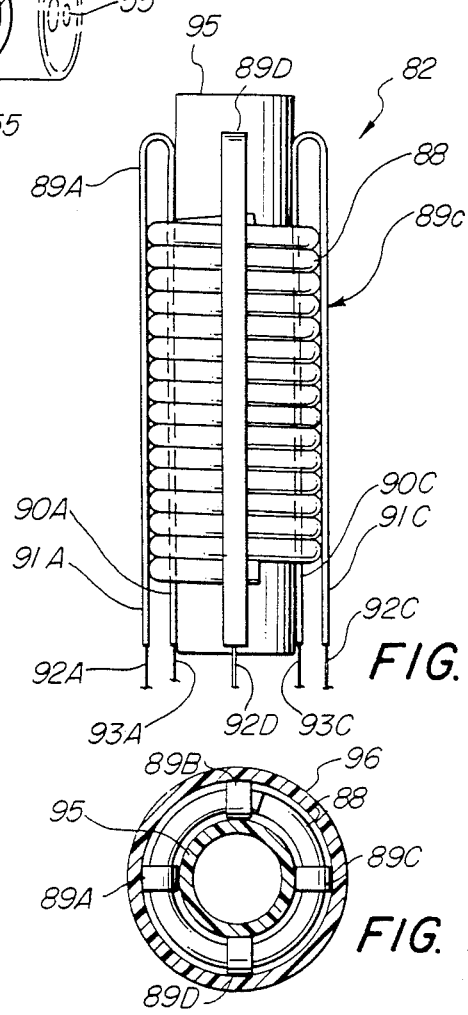
FIG. 11 is a side elevation view of a four-way, double plane articulating assembly similar to the two-way assembly shown in FIG. 9.
Figure 12:
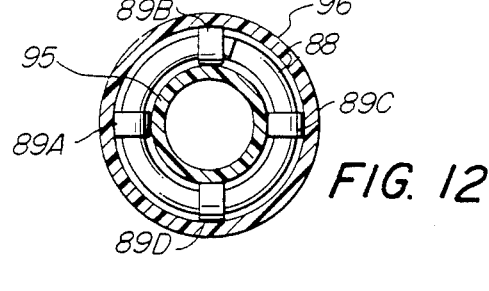
FIG. 12 is a front end view of the apparatus of FIG. 9 with alternate articulated positions of the borescope head shown in phantom.

In another embodiment of the actuator 52 shown in FIGS. 9 and 10, a second pair of longitudinal zone strip heaters is added. Thus, as shown in FIGS. 11 and 12, actuator 82 is similar in construction to actuator 52, having a helical SME alloy spring 88, a hollow rubber core tube 95, and a flexible cylindrical jacket 96. Actuator 82 also includes a first flexible strip heater 89A, having an inner half 90A, an outer half 91A, and conductor leads 92A and 93A.

A second flexible strip heater 89B is looped around the helical spring 88, in a position diametrically opposed to the first strip heater 89A, and has analogous elements 90B, 91B, 92B and 93B.

A third flexible strip heater 89C is looped around helical spring 88, at the mid point between strip heaters 89 and 89B, i.e., at a 90° circumferential angle with respect to the latter two strip heaters. The third flexible strip heater 89C has elements 90C, 91C, 92C and 93C corresponding to the same numbered elements of the first and second heater elements.

A fourth flexible strip heater 89D is looped around helical spring 88 in a position diametrically opposed to the position of the third strip heater 89C, and has analogous elements 90D, 91D, 92D and 93D.

Actuator 82 may be flexed either way in two perpendicular planes bisecting the opposed pairs of heater strips 89A, 89B, 89C and 89D by selectively energizing the heater strips, in a manner exactly similar to that described for the single plane articulation apparatus actuator 52. Thus, articular 82 provides a two-way, two-plane articulation capability for borescope tips.

In principle, more than two pairs of strip heaters of the type described above could be added to our actuators to increase the number of planes of articulation capability. However, these additional planes of articulateability can be more readily added in other embodiments of our articulation apparatus to be described below.

Figure 13:
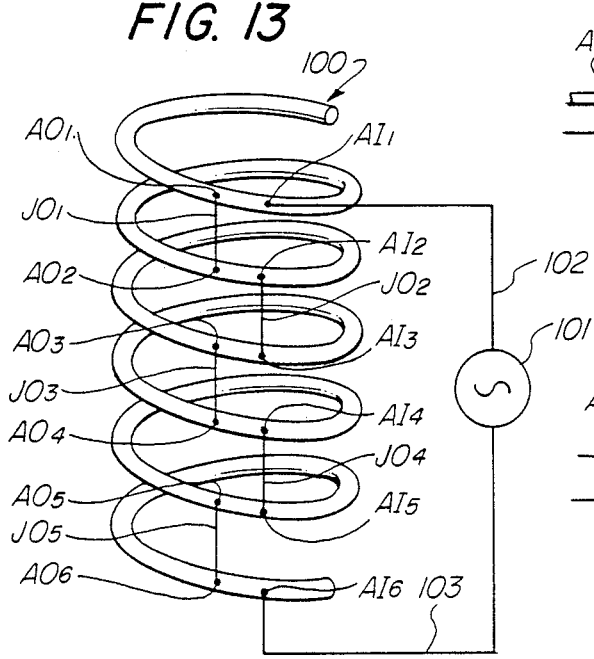
FIG. 13 is a fragmentary, partially schematic perspective view of an alternate means of heating a selected longitudinal zone of actuator springs of the type shown in FIGS. 5, 9 and 11.

FIG. 13 illustrates an alternate means of heating a selected longitudinal zone of a helical SME alloy actuator spring of the type shown in FIGS. 5, 9 and 11 and described above. The heating method shown in FIG. 13 employs electrical current flowing directly through portions of the SME alloy wire of which the helical actuator spring is fabricated. Direct heating is particularly well suited for use with NI—TI (NITINOL) wires, since the relatively high electrical resistivity of that material permits self heating the wires with relatively modest currents. (The volume resistivity of NITINOL is of the order of $30 \times 10^{-6}$ OHM-inch, versus $3 \times 10^{-6}$ OHM-inch for CU—ZN—AL SME alloys.)

As shown in FIG. 13, a helical spring 100 is fabricated from NITINOL wire and imprinted with an elongated high temperature memory shape. A controllable source of electrical current 101 is interconnected to spring 100 in a manner which will now be described. Controllable electrical current source 101 may be either an alternating current source, as shown in FIG. 13, or a direct current source.

One terminal of the current source 101 is connected by a flexible electrical conductor 102 to a point AI1, on an upper coil of helical joined to NITINOL spring 100. Joined to a second point A01 on the same coil of the helical spring 100 is a flexible electrical conductor J01. Conductor J01 runs directly downward from point A01 on the upper or first coil of the helical spring 100 to connect electrically to point A02 on the second coil of the spring. Point A02 is in vertical alignment with point A01 on the first coil of the helical spring 100. Joined to a second point AI2 on the second coil of the helical spring 100 is a flexible electrical conductor J02. Point AI2 is vertically aligned with point AI1 on the first coil of the helical spring 100. Thus, the arcs between connection points AI and AO on coils 1 and 2 of helical spring 100 form parallel, vertically aligned segments of the spring, defining a longitudinal zone along a side of the spring.

As shown in FIG. 13, additional flexible jumper conductors join vertically aligned connection points on the third and successive coils of spring 100. At the last or lowest desired loop N of spring 100, a flexible electrical conductor 103 joins point AIN (AI6 in FIG. 13) to the second terminal of current source 101.

Figure 14:
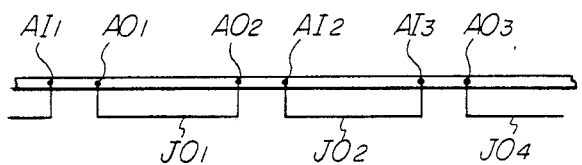
FIG. 14 is a diagrammatic view of the device of FIG. 12.
Figure 15:
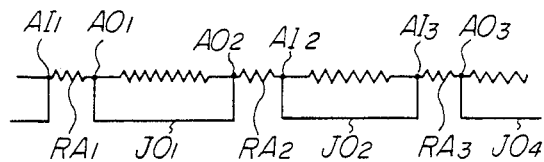
FIG. 15 is a schematic view of a circuit equivalent to the structure shown in FIG. 13.

FIG. 14 is a diagrammatic view of the apparatus of FIG. 13 in which the helix has been mapped into a straight wire. FIG. 15 is an equivalent electrical circuit corresponding to FIG. 14. As shown on FIGS. 14 and 15, current flowing into terminal AI1 and out of terminal AIN is effective in heating longitudinally aligned arcs of spring 100 designated RA1, RA2, RAN in FIG. 15. Thus, a current source 101, connected in series with a coil 100 interconnected by jumper wires JN as shown in FIGS. 13, can be used to heat selected longitudinally aligned segments of spring 100. When the resistive self-heating of the segments is sufficient to raise the temperature of the longitudinal zone of the spring 100 defined by the segments to the transition temperature of the SME alloy, spring 100 will be deflected towards the heated zone.

Figure 16:
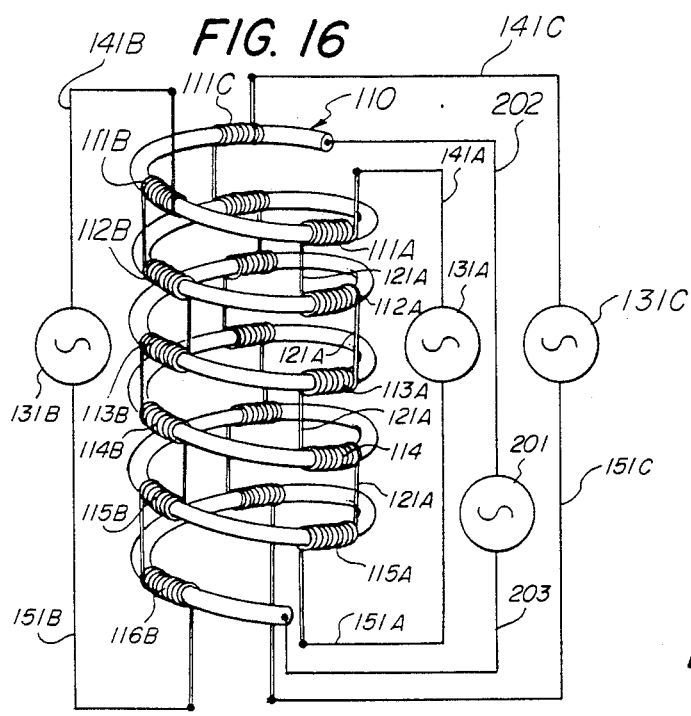
FIG. 16 is a fragmentary, partially schematic view of another means for differentially heating selected longitudinal zones of actuator springs of the type shown in FIGS. 5, 9, and 11.

FIG. 16 illustrates means for differentially heating selected longitudinal zones of an SME alloy spring of any composition. In FIG. 16, an SME alloy helical spring 110 of any suitable composition has coils of resistance heating wire encircling selected arc segments of loops of the spring. The resistance heating wire is made from a material of relatively high resistivity, such as NICHROME, and is covered with an electrically insulating coating such as enamel.

As shown in FIG. 16, heating coils 111A through 115A are wound around vertically aligned arc segments of adjacent loops of the helical spring 110 Adjacent coils are interconnected in series by flexible jumper wires 121A. The free end of the first coil 111A is connected to a first terminal of a controllable current source 131A by an insulated connecting wire 141A. The free end of the last coil 115A is connected to a second terminal of the controllable current source 131A by an insulated connecting wire 151A.

When sufficient current is supplied to heating coils 111A through 114A by the controllable current source 131A to heat arc segments of the SME alloy articulator spring to the transition temperature of the alloy, the spring will be deflected towards the longitudinal zone defined by the longitudinally aligned heater coils.

If actuation of the SME alloy helical actuator spring in more than one direction is required, additional columns of vertically aligned heater coils may be wound around arc segments of adjacent spring loops spaced apart circumferentially from the heater coils 111A–114A. Thus, an additional column of heater coils 111B–114B may be wound around adjacent loops of the helical spring 110, in a longitudinally aligned column spaced 120 degrees clockwise around a coil of the spring from the column comprised by coils 111A–114A. These heating coils 111B–114B are energizable by a second controllable current source 131B connected in series with the coils by means of connecting wires 141B and 151B, and jumper wires 121B.

A third plane of articulation capability may be added to the articulation mechanism of FIG. 16 by adding a third column of heater coils 111C–114C, energized by a third controllable current source 131C connected in series with the heater coils by means of connecting wires 141C and 151C, and jumper wires 121C. In an exactly analogous fashion, additional planes of articulation capability may be provided by adding additional columns of heating coils.

Although jumper wires 121 are shown in FIG. 16 to run longitudinally between corresponding points on adjacent coils 111–114 in a column, longer jumper wires which parallel the SME alloy wire forming the helical spring 110 could be used in place of the longitudinally oriented jumper wires.

In the actuation configuration shown in FIG. 16 as well as in previously described embodiments of our SME alloy actuators, selected portions of the SME alloy actuator element must be controllably heated to raise the temperature of the alloy to its transition temperature to force the actuator element into a first memory shape, and then cooled to permit the element to assume a quiesient shape. Although the heat energy required to effect the shape transition may be supplied entirely by a single heating means such as heater coils 111–114 in FIG. 16, it is advantageous for some applications to supply a portion of the heat energy required from auxiliary means. For example, if we assume that the transition temperature range of the SME alloy spring 110 in FIG. 16 is 160° F. to 180° F., heating the entire spring to a temperature slightly below the transition temperature 140° F., for example, would permit differential articulation of the spring with smaller currents through heating coils 111–114.

One way to bias the entire actuator spring to a temperature between ambient and the transition temperature is to blow warm air through the spring. Another way would be to connect the spring to a heat source. A third way is to uniformly heat the entire spring by means of current flowing through the spring. Thus, as shown in FIG. 16, a separate controllable current source 201 may be connected to opposite ends of the helical spring 110 by means of connecting wires 202 and 203, thus providing means for direct resistive heating of the spring. This direct heating method is particularly well suited to relatively high resistivity SME alloys such as NITINOL. Preferably, a temperature sensor such as a thermistor is placed in thermal contact with the spring 110 and used to provide a feedback signal to the controllable current source 201, permitting precise closed-loop command of desired temperatures of the spring.

Figure 17:
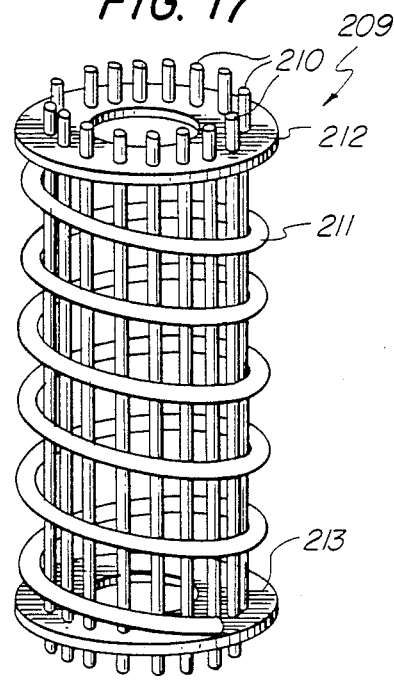
FIG. 17 is a perspective view of another means for differentially heating selected longitudinal zones of actuator springs of the type shown in FIGS. 5, 9 and 11 in which straight heating elements are used.
Figure 18:
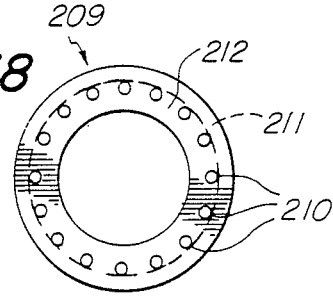
FIG. 18 is a front end view of the apparatus of FIG. 17.

FIGS. 17 and 18 illustrate another apparatus 209 for heating selected longitudinal zones of a SME alloy, helical actuator spring. In the embodiment shown in FIGS. 17 and 18, a plurality of parallel, flexible heater wires 210 arranged in a circle of the same diameter as the inner diameter of an SME alloy helical spring 211 runs longitudinally through the center of the spring. Heater wires 210 are in close thermal contact with the inner circumferential surfaces of the loops of spring 211, and extend slightly beyond the top and bottom loops of the spring when it is at its maximum extension. The heater wires 210 are anchored at their upper ends to an annular-shaped, upper insulating support plate 212, and at their lower ends to an annular-shaped, lower insulating support plate 213. Selectively energizing one or more of the heater wires 210 by an external current source permits raising the temperature of selected longitudinal zones of the spring 211 to the transition temperature of the SME alloy, thereby effecting articulation of the spring towards the heated zone.

FIGS. 19 and 20 illustrate another apparatus 219 for heating selected longitudinal zones of an SME alloy, helical actuator spring. The embodiment shown in FIGS. 19 and 20 also employs a plurality of parallel, flexible heater wires 220 to heat a helical SME alloy actuator spring. Heater wires 220 are arranged in a circle of a diameter equal to the mean of the inner and outer diameters of the helical spring 221. Each of the heater wires 220 runs longitudinally through a separate column of longitudinally aligned holes 222 through adjacent loops of the helical spring 221. A plurality of such columns of holes are regularly spaced around the upper circumferential surface of each loop of the hilical spring 221. The heater wires 220 are sufficiently long to extend slightly beyond the top and bottom loops of the spring 221 when it is at its maximum extension. The heater wires 220 are anchored at their upper ends to an annular-shaped upper insulating support plate 223, and at their lower ends to an annular-shaped, lower insulating support plate 224. Selectively energizing one or more of the heater wires 220 by an external current source permits raising the temperature of selected longitudinal zones of the spring 221 to the transition temperature of the SME alloy, thereby effecting articulation of the spring towards the heated zone.

FIGS. 21 and 22 show another apparatus 239 for heating selected longitudinal zones of an SME alloy helical actuator spring. In this embodiment, a plurality of straight, flexible heater wires 240 are arranged in a circle of the same diameter as an SME alloy spring 241. The spring 241 has a generally helical shape. However, in forming the spring, small, single-turn minor loops 242 having approximately the same diameter as the heater wires 240 are formed at regular circumferential angles within the major loop of the spring.

The minor loops 242 in adjacent major loops of the spring 241 are longitudinally aligned. Thus, each longitudinal column of minor loops 242 forms a hollow conduit adapted to receive a separate one of the heater wires.

The heater wires 240 are sufficiently long to extend slightly beyond the top and bottom major loops of the spring 241 when it is at its maximum extension. The heater wires 240 are anchored at their upper ends to an annular-shaped, upper insulting support plate 243, and at their lower ends to an annular-shaped, lower insulting support plate 244. Selectively energizing one or more of the heater wires 240 by an external current source permits raising the temperature of selected longitudinal zones of the spring 241 to the transition temperature of the SME alloy, thereby effecting articulation of the spring towards the heated zone.

A borescope articulation apparatus employing a single, uniformly heated helical spring fabricated from an SME alloy is shown on FIGS. 23, 24 and 25.

As shown in FIG. 23, borescope articulation apparatus 250 includes an upper cylindrical section 251 coaxially aligned with a lower cylindrical section 252, and spaced longitudinally above the lower cylindrical section. An elongated, longitudinally disposed support member 253 extends upward from the cylindrical wall of the lower cylindrical section 252. A pivotable joint 254 joins the upper end of the support member 253 to the lower end of the cylindrical wall of the upper cylindrical section 251.

An annular-shaped, upper end plate 255 caps the upper end of lower cylindrical section 252. A similar annular-shaped, lower end plate 256 caps the lower end of upper cylindrical section 251. A helical SME alloy spring 257 is fastened at its upper end to the lower annular end plate 256 of the upper cylindrical section 251, and at its lower end to the upper annular end plate 255 of the lower cylindrical section 252. The longitudinal axis of the spring 257 is in parallel alignment with elongated support member 253, and positioned on the diametrically opposite side of the lower annular end plate 255.

The lower cylindrical section 252 of the articulation apparatus 250 is secured coaxially around the flexible cable 258 of a borescope 259. The upper cylindrical section 251 is secured coaxially around the cylindrical tip 260 of the borescope 259. A convoluted, bellows-shaped boot 261 made of an elastomeric material is joined coaxially to the outer cylindrical walls of lower cylindrical section 252 and upper cylindrical section 251, spanning the space between those two sections and providing an enclosure for the moving elements of apparatus 250.

Electrical conductors 262 and 263 connected to the upper and lower ends, respectively of the spring 257 pass through the lower cylindrical section 252 to a controllable external source of electrical current.

With no heating current applied to spring 257, it is completely compressed at ambient temperature, as shown in FIG. 23. Introducing sufficient heating current into the spring 257 to raise the temperature of at least part of the spring to the lower threshold of the transition region causes the spring to expand to the position shown in FIG. 24. Increasing the temperature further causes the spring 257 to recover fully its memory shape, as shown in FIG. 25.

Figure 26:
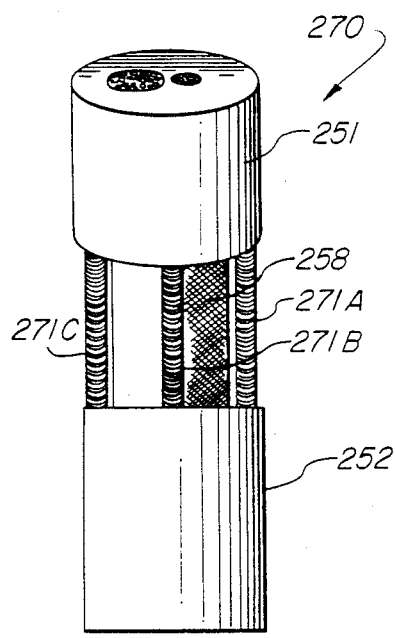
FIG. 26 is a perspective view of a borescope articulation apparatus according to the present invention which employs a plurality of SME alloy spring actuators which may be separately heated to a different temperature.
Figure 27:
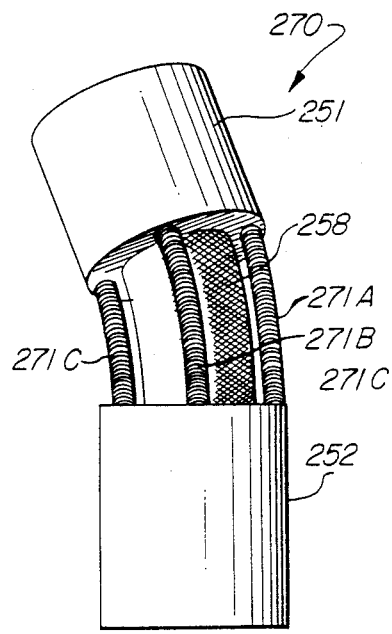
FIG. 27 is a perspective view of the apparatus of FIG. 26 in which one actuator spring has been heated above its transition temperature.
Figure 28:
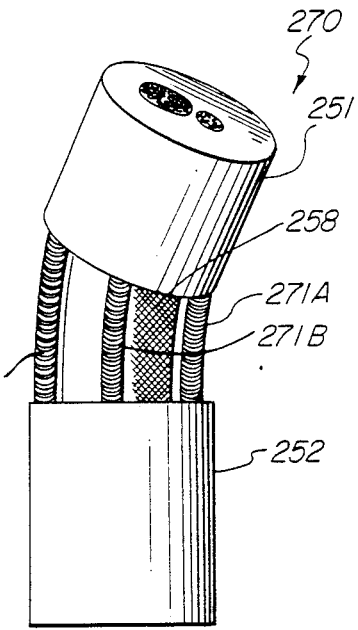
FIG. 28 is a perspective view of the apparatus of FIG. 26 in which a different actuator spring has been heated above its transition temperature.

FIGS. 26 through 28 illustrate a variation of the embodiment of the articulation apparatus shown in FIGS. 24 through 25. In the embodiment 270 shown in FIGS. 26 through 28, three springs 271A, 271B and 271C spaced at 120° intervals are used to provide a three plane articulation capability. However, the apparatus 270 shown in FIGS. 26 through 28 is capable of directing the aim point of the borescope to any point in space, rather than being confined to three planes. This is possible because simultaneous differential extension of more than one spring results in a vector sum bending moment which may be in any arbitrary, intermediate plane.

Figure 29:
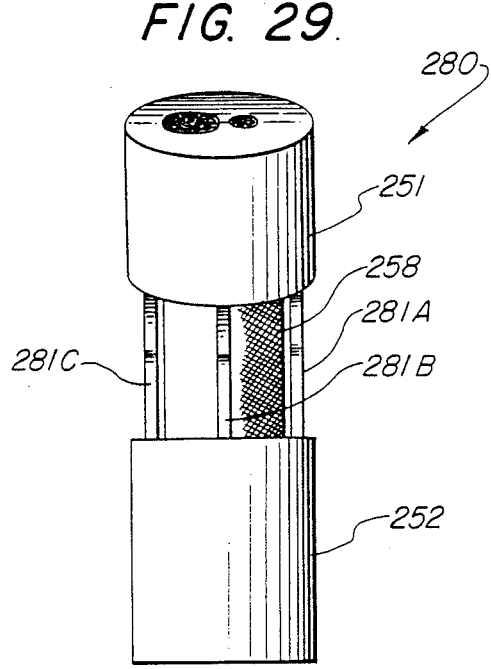
FIG. 29 is a perspective view of another embodiment of the present invention which employs solid rods rather than springs.
Figure 30:
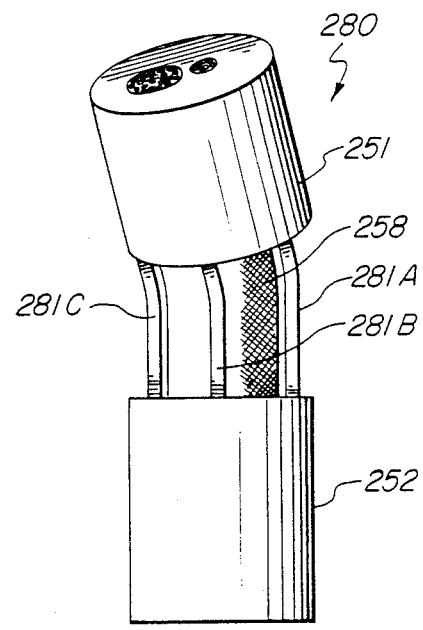
FIG. 30 is a perspective view of the apparatus of FIG. 29 in which one actuator rod has been heated above its transition temperature.

FIG. 29 and 30 illustrate another embodiment 280 of the articulation apparatus according to the present invention in which SME alloy rods 281A, 281B and 281C trained to have one-way or two-way memory are used as actuator elements in place of helical sprigns.

SME alloy rods may also be trained to have memory of a particular torsional angle, or twist, about the longitudinal axis of the rod. If such a rod is disposed between a borescope tip and cable in a position displaced from the optical axis of the tip, heating the rod to its transition temperature can rotate the line of sight of the tip a desired amount.

What is claimed is:

1. An apparatus for spatially orienting the pointing direction of a movable distal end of an elongated structure comprising:
    (a) a shape memory effect alloy actuator connected between said distal end of said elongated structure and an intermediate portion of said elongated structure, said actuator having at least one, first memory shape capable of deflecting said movable end of said elongated structure, and
    (b) means for varying the temperature of said actuator from a quiescent value to a value which effects a shape transition of said actuator proportional to said temperature variation, said means being controllable from the proximal end of said elongated structure.

2. The apparatus of claim 1 wherein said first memory shape of said shape memory effect alloy actuator is recovered, with the production of force sufficient to perform external work, from a first quiescent shape when the temperature of said actuator is varied to approach the transition temperature of said alloy, the degree of said first memory shape recovery being proportional to the closeness of the actual temperature of said actuator to its transition temperature.

3. The apparatus of claim 2 wherein said means for varying the temperature of said actuator is further defined as being capable of circumferentially differentially heating a selected zone of said actuator.

4. The apparatus of claim 2 wherein said shape memory effect alloy is chosen from the group of alloys comprising nickle-titanium, cooper-zinc-aluminum and copper-zinc-tin.

5. The apparatus of claim 2 further comprising means for forcing said actuator into a quiescent shape upon decreasing the temperature of said actuator below its transition temperature.

6. The apparatus of claim 5 wherein said means for forcing said actuator into a quiescent shape upon decreasing the temperature of said actuator below its transition temperature comprises an external spring bias means.

7. The apparatus of claim 5 wherein said means for forcing said actuator into a quiescent shape upon decreasing the temperature of said actuator below its transition temperature comprises previously training second actuator to assume a second memory shape when cooled below its transition temperature, said second memory shape being recovered with the production of force sufficient to perform external work.

8. The apparatus of claim 5 wherein said actuator is further defined as comprising at least one helical spring fabricated from a shape memory effect alloy and having a first memory shape previously imprinted on said spring.

9. The apparatus of claim 8 wherein at least one of said helical springs has a second memory shape previously imprinted on said spring.

10. The apparatus of claim 5 wherein said actuator is further defined as comprising at least one elongated member fabricated from a shape memory effect alloy and having a first memory length imprinted on said elongated member.

11. The apparatus of claim 10 wherein at least one of said elongated members has a second memory length imprinted in said elongated member.

12. The apparatus of claim 5 wherein said actuator is further defined as comprising at least one elongated member fabricated from a shape memory effect alloy and having a first bent memory shape imprinted on said elongated member.

13. The apparatus of claim 12 wherein at least one of said elongated members has a second bent memory shape imprinted on said elongated member.

14. The apparatus of claim 5 wherein said actuator is further defined as comprising at least one member fabricated from a shape memory effect alloy and having a first twisted memory shape characterized by a first torsional angle.

15. The apparatus of claim 14 wherein at least one of said members has a second twisted memory shape characterized by a second torsional angle.

16. An apparatus for spatially orienting the pointing direction of the distal end of a flexible borescope comprising:
(a) at least one helical spring fabricated from a shape memory effect alloy, said spring being attached to both the cable and tip of said borescope, and said spring having memory of at least a first shape previously imprinted upon said spring, and
(b) means for varying the temperature of at least part of said spring to approach the transition temperature of the said shape memory effect alloy of which said spring is fabricated, whereby said spring shape may approach its memory shape with an accompanying production of external force effective in moving said borescope tip relative to said borescope cable, the closeness of approach of said spring shape to its memory shape being proportional to the closeness of the actual temperature of said spring to said transition temperature of said spring.

17. The apparatus of claim 16 wherein said helical spring is longitudinally disposed between the front transverse face of said borescope cable and the rear transverse face of said borescope tip, the longitudinal axes of said borescope tip and said borescope cable being aligned, and the longitudinal axis of said helical spring being displaced from and parallel to said common axes of said borescope tip and cable.

18. The apparatus of claim 17 further comprising a pivotable joint disposed between the rear face of said borescope tip and the front face of said borescope cable.

19. The apparatus of claim 16 wherein the longitudinal axis of said helical spring is coaxial with the axes of said borescope tip and said borescope cable.

20. The apparatus of claim 19 wherein said means for varying the temperature of said spring is further defined as being capable of differentially heating a selected zone of said spring.

21. The apparatus of claim 20 wherein said spring is further defined as having a first memory shape at the transition temperature of said alloy characterized by a first elongation, and a quiescent shape at a temperature below said transition temperature characterized by a second elongation.

22. The apparatus of claim 21 wherein said spring is forced into said quiescent shape upon decreasing the temperature of said spring below its transition temperature by means of auxiliary spring bias means.

23. The apparatus of claim 21 wherein said spring is further defined as having a second memory shape at temperatures below said transition temperature of said alloy characterized by a second elongation.

24. The apparatus of claim 21 wherein said means for differentially heating said spring is further defined as being capable of selectably heating a selected longitudinal zone of said spring to the transition temperature of said alloy, thereby causing said spring to bend in a longitudinal plane containing the longitudinal axis of said spring.

25. The apparatus of claim 24 wherein said means for differentially heating a selected longitudinal zone of said spring is further defined as an electrical heating element in thermal contact with said selected longitudinal zone.

26. The apparatus of claim 25 further comprising means for bringing said spring to a uniform selected temperature.

27. The apparatus of claim 26 wherein said means for bringing said spring to a uniform selected temperature comprises a source of air of controllable temperature and flow rate flowing by said helical spring.

28. An apparatus for deflecting the tip of a borescope at the end of a flexible cable to point in a desired direction comprising:
(a) at least one helical spring fabricated from a shape memory effect alloy and having a memory of at least one shape imprinted on said spring, said shape being recoverable with the production of accompanying external force when at least part of said spring is heated to the transition temperature of said shape memory effect alloy of which said spring is fabricated, the degree of completeness of said shape recovery being proportional to the closeness of the actual temperature of said spring to said transition temperature of said spring,
(b) means for restoring said spring to a quiescent, second shape when said spring is cooled below said transition temperature,
(c) means for coupling said shape transitions to said borescope tip and cable effective in moving said tip relative to said cable,
(d) means for heating said spring to approach said transition temperature as closely as desired, and
(e) means for cooling said spring to a temperature below said transition temperature.

29. The apparatus of claim 28 wherein said means for heating said spring is further defined as being capable of differentially heating a selected part of said spring.

30. The apparatus of claim 29 wherein said means for differentially heating said spring comprises at least one electrical resistance heating unit in thermal contact with a selected zone of said spring, and means for providing flow of a controlled amount of electrical current through said heating unit.

31. The apparatus of claim 30 wherein said heating unit comprises an elongated insulated strip containing internal resistance wire heating elements, said strip being disposed in thermal contact with a selected longitudinal zone of said spring.

32. The apparatus of claim 31 wherein said heating unit is further defined as having an elongated U-shape at least partially enclosing a selected longitudinal zone of said spring.

33. The apparatus of claim 30 wherein said heating unit comprises at least one coil of insulated electrical resistance wire wrapped around at least part of at least one loop of said spring.

34. The apparatus of claim 30 wherein said heating unit comprises in combination at least one electrically conductive segment of at least one loop of said spring, an electrical input terminal connected to one end of said segment and an electrical output terminal connected to the other end of said segment, whereby electrical current induced to flow through said segment by connection of a source of electromotive force between said input and output connections results in resistive heating of said segment.

35. The apparatus of claim 30 wherein said heating unit comprises at least one elongated, flexible resistance heating wire disposed longitudinally through the center aperture of said spring in close thermal contact with the inner circumferential surfaces of the loops of said spring.

36. The apparatus of claim 30 wherein said heating unit comprises in combination at least one column of longitudinally aligned holes through adjacent loops of said spring, and at least one elongated, flexible resistance heating wire disposed longitudinally through each said column of longitudinally aligned holes.

37. The apparatus of claim 30 wherein said heating unit comprises in combination at least one column of longitudinally aligned smaller diameter, single turn minor loops in each major loop of said spring, and at least one elongated, flexible resistance wire disposed longitudinally through each said column of longitudinally aligned, single turn minor loops in said spring.

38. In a structure having a body and an end part movable with respect to said body, the method of moving said movable part to point in an arbitrary desired direction with respect to said body comprising:
(a) connecting an actuating member fabricated of a shape memory effect alloy between said body and movable end part of said structure, and
(b) varying the temperature of said actuating member to approach a value at which at least part of said actuating member approaches a transition to a memory shape.

39. The method of claim 38 wherein a selected portion of said actuating member is brought to said transition temperature.

40. The method of claim 38 wherein the temperature of said actuating member is varied by energizing electrical heaters in thermal communication with said actuating member.

41. The method of claim 40 wherein the temperature of said actuating member is sequentially varied by energized thermoelectric coolers in thermal communication with said actuating member.

42. The method of claim 38 wherein the temperature of said actuating member is varied by flowing fluid in thermal contact with said actuating member by said member, and controlling the temperature and flow rate of said fluid.

* * * * *